United States Patent [19]

Glover

[11] 4,034,757

[45] July 12, 1977

[54] DISPENSER FOR PHARMACEUTICALS HAVING PATIENT COMPLIANCE MONITOR APPARATUS

[75] Inventor: Frederick Flagg Glover, Palo Alto, Calif.

[73] Assignee: Alza Corporation, Palo Alto, Calif.

[21] Appl. No.: 696,664

[22] Filed: June 16, 1976

[51] Int. Cl.$^2$ .................... A61M 31/00; B67D 5/22

[52] U.S. Cl. ............................... 128/260; 128/213; 222/30; 222/36; 222/70

[58] Field of Search ............. 128/260, 213; 222/30, 222/36, 70, 153

[56] References Cited

U.S. PATENT DOCUMENTS

| | | | |
|---|---|---|---|
| 3,170,597 | 2/1965 | Richenberger | 222/36 |
| 3,257,034 | 6/1966 | Dumm | 222/36 |
| 3,386,621 | 6/1968 | Arps et al. | 222/30 |
| 3,845,883 | 11/1974 | Johnson et al. | 222/30 |

*Primary Examiner*—Aldrich F. Medbery

*Attorney, Agent, or Firm*—Thomas H. Olson

[57] ABSTRACT

An impervious housing having a compartment for a pharmaceutical product and an independent compartment for containing circuitry that senses and records when a patient administers the pharmaceutical contained in the first compartment. The circuit includes a clock which produces a pulse each hour and an addressable memory coupled to the clock so that the address is changed each hour. Sensors for determining when the cap is removed from the first compartment and when the housing is inverted, the output of the sensors being coupled to a register at the input of the circuitry so that if a patient has administered the pharmaceutical since the last clock pulse, a binary signal indicative of that fact will be transferred from the register to the memory upon occurrence of a succeeding clock pulse.

8 Claims, 3 Drawing Figures

DISPENSER FOR PHARMACEUTICALS HAVING PATIENT COMPLIANCE MONITOR APPARATUS

BACKGROUND OF THE INVENTION

1. Field of the Invention

This invention relates to a container for pharmaceuticals and more particularly to a container having self-contained circuitry for recording each instance of administration of the pharmaceutical by a patient and the time of such administration.

2. Description of the Prior Art

In an article entitled "Medication Monitor for Ophthalmology" by Yee et al. published in the American Journal of Ophthalmology, Volume 78, No. 5, November 1974, there is described a housing having an electronic counter circuit therein and a compartment in which a vial of ophthalmic solution is stored. When the bottle of ophthalmic solution is removed such removal is stored in the counter as an event. The described apparatus is accurate so long as the pharmaceutical bottle is returned to the compartment each time after use, a condition which cannot be relied on for all patients in all circumstances.

SUMMARY OF THE INVENTION

The efficacy of a given regimen of treatment is in large part dependent upon patient compliance with dosage instructions. Accurate information on patient compliance is essential in accurately evaluating the efficacy of a prescribed regimen.

Accordingly it is an object of this invention to provide a pharmaceutical container from which it is difficult if not impossible to dispense the contents without recording occurrence of such event.

Another object of the invention is to provide a container of the type referred to above in which the likelihood of false signals in minimized, if not eliminated. This object is achieved by providing two transducers and by recording as an event only those instances when both transducers are activated. One transducer is activated when the cap is removed and the other transducer is activated only when the container is inverted. No signals are produced if only one of the two conditions exists at any time, wherefore the container can be carried on the person of the patient without risk of false signals.

A further object is to provide a device of the type described wherein the compartment containing the pharmaceutical is independent from the compartment containing the circuit elements in order to preserve sterility of the pharmaceutical material. This object is achieved by providing a container wherein the circuit containing compartment is accessible even after the pharmaceutical compartment is sterilized and sealed.

Still another object of the invention is to provide a device of the type described wherein the data stored in the memory in the device can be read out at a rapid rate. This object is achieved by providing circuitry which permits connection of an external clock pulse which typically has a much higher repetition rate than the once per hour repetition rate of the internal clock.

Yet another object is to provide a device of the type described wherein the relatively expensive circuit elements can be removed and reused numerous times. This object is achieved by forming the circuitry compartment independent of the pharmaceutical containing compartment and by affording access to the circuit containing compartment at a location remote from the closable opening from which the pharmaceutical is dispensed.

The foregoing, together with other objects, features and advantages, will be more apparent after referring to the following specification and the accompanying drawings.

DESCRIPTION OF THE PREFERRED EMBODIMENT

Figure 2:
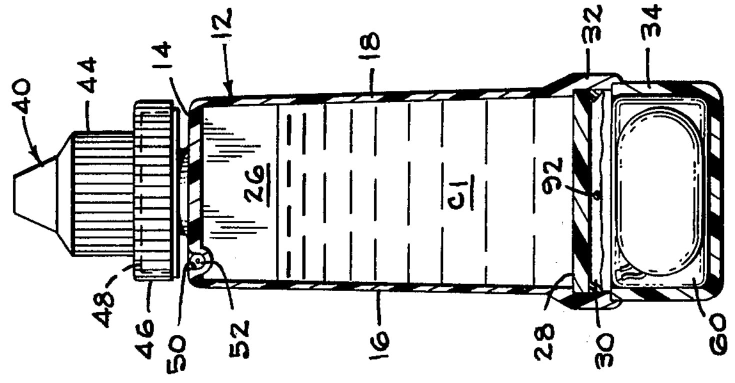
FIG. 2 is a cross-sectional view taken on a plane designated by line 2—2 of FIG. 1.

Referring more particularly to the drawings, reference numeral 12 indicates a housing embodying the invention. Housing 12 has a top wall 14, side walls 16 and 18, and end walls 20 and 22 which can be integrally molded of suitable synthetic resinous or plastic material. Also integrally molded with the top, side and end walls are laterally extending transverse walls or partitions 24 and 26. The volume defined between the central portion of side walls 16 and 18 and partitions 24 and 26 defines a compartment $C_1$ for containing the pharmaceutical preparation, e.g. ophthalmic drops or the like. The compartment is completed by a bottom panel 28 which is retained in place by a bead of adhesive 30 or the like.

Circumscribing the lower extremity of side walls 16 and 18 and end walls 20 and 22 is a flange 32 which is adapted to receive a bottom closure member 34. The closure member telescopes into flange 32 and defines hollow cavities $C_{2a}$, $C_{2b}$ and $C_{2c}$ that are disposed within housing 12 outward of transverse walls 24 and 26. Cavities $C_{2a}$, $C_{2b}$ and $C_{2c}$ constitute a compartment which is independent of compartment $C_1$. Extending upward from top wall 14 is an externally threaded neck 36 which defines a passage 38 communicating compartment $C_1$ to the exterior of housing 12 so as to permit dispensing of the pharmaceutical contained within the compartment. Within passage 38 is disposed a metering tip to facilitate control by the patient of the amount of the pharmaceutical dispensed from compartment $C_1$. For closing passage 38 during storage and transportation of the housing there is a cap 40 having a core 42 which is internally threaded to cooperate with externally threaded neck 36 so as to retain the cap in place. Cap 40 has a cover 44 suitably secured to core 42, the cover 44 having an outwardly flared base portion 46 which defines an annular cavity for containing an annular magnet 48, the purpose of which will be made apparent subsequently.

Top wall 14 defines a slot 50 adjacent neck 36 in which is disposed a magnetic reed switch 52. The opposite ends of slot 50 have holes 54 and 56 for communicating the leads of the reed switch with respective cavities $C_{2b}$ and $C_{2c}$. Slot 50 is so disposed relative the position of annular magnet 48 when cap 40 is threaded onto neck 36 that the contacts of switch 52 are closed by the flux produced by the magnet. When the cap is removed so as to separate annular magnet 48 from reed switch 52, the contacts of the reed switch open.

Figure 1:
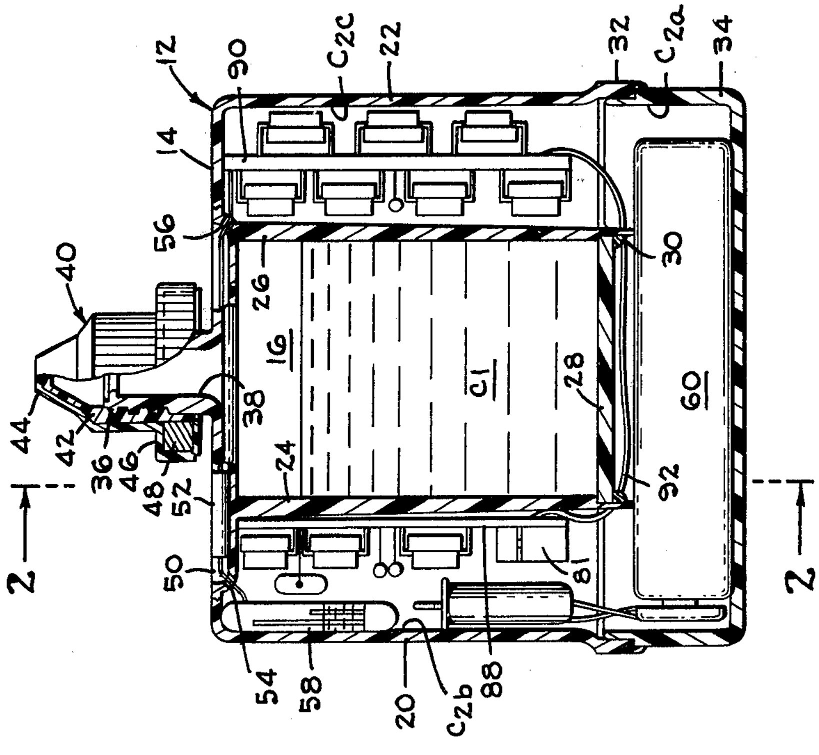
FIG. 1 is a side elevation view in cross section of a container embodying the invention.

The specific physical arrangement of the circuit elements within cavities $C_{2b}$ and $C_{2c}$ is not critical with the exception of the location of a mercury switch 58 which constitutes an element of the counter circuit. As can be seen in FIG. 1, in which housing 12 is in an upright position, mercury switch 58 is oriented so that in such position the mercury contained therein will bridge the two contacts to form a closed circuit whereas when the housing is inverted with neck 36 below compartment $C_1$, the contacts will become open circuited by movement of the mercury away from such bridging relation in response to the force of gravity acting on the mercury.

Figure 3:
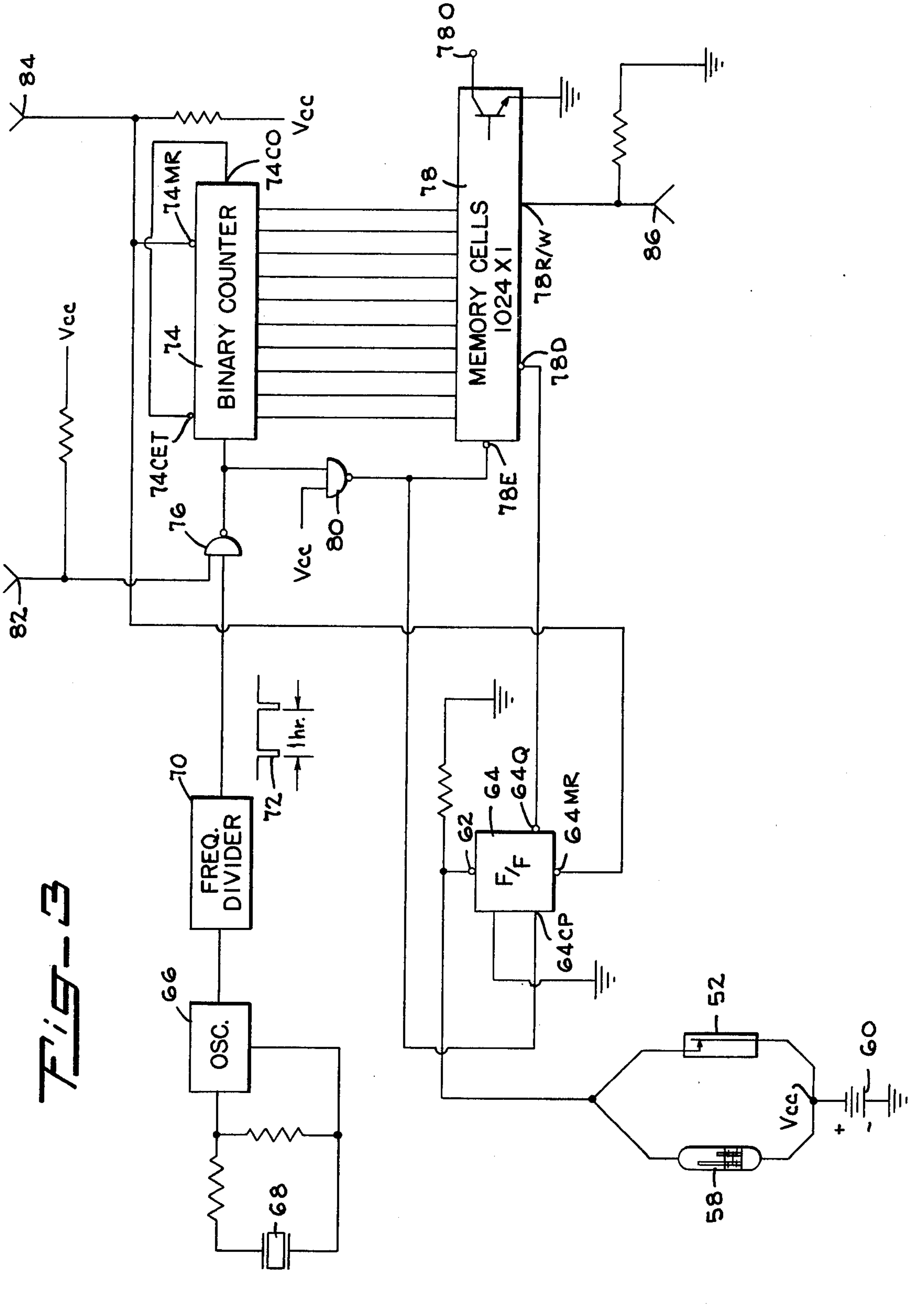
FIG. 3 is a schematic block diagram of the counter and memory circuitry employed in the present invention.

Referring to FIG. 3 the contacts of reed switch 52 and mercury switch 58 constitute the event inputs to the counter circuit. The contacts of the reed switch and mercury switch are connected in parallel with one another between the positive terminal $V_{cc}$ of the battery 60 and a preset terminal 62 of a D-type flip-flop 64 which functions as a data latch. The negative terminal of battery 60 is grounded.

Flip-flop 64 constitutes the data input for the counter circuit that constitutes an element of the invention. The counter circuit includes an oscillator 66, the frequency of which is controlled by a crystal 68. In one circuit designed according to the invention, oscillator 66 is caused by crystal 68 to oscillate at a frequency of 18.647 kHz which frequency is reduced by a frequency divider 70 so as to produce a series of clock pulses 72 at one hour intervals. The clock pulses drive a binary counter 74 through a NAND gate 76. Accordingly, binary counter 74 advances one count for each hour. The output of binary counter 74 is connected in accordance with well understood and conventional procedures to a memory 78 so that once each hour a unique cell within the memory is addressed.

The output of NAND gate 76 is also connected to the input of a NAND gate 80, the output of which is connected to the enable terminal 78E of memory 78 and to a clock pulse terminal 64 CP of flip-flop 64. As will appear in more detail hereinafter, NAND gate 80 functions as a delay so that before data from flip-flop 64 is inputted to memory 78, binary counter 74 advances one count to address the correct location within the memory. The output of flip-flop 64 appears at a terminal 64Q which is connected to the data input terminal 78D of the memory.

In one system designed according to the present invention memory 78 has a capacity of 1,024 addressable memory locations or cells, binary counter 74 having a similar capacity. Thus because clock pulse 72 occurs at a one hour repetition rate, the time capacity of memory 78 represents more than 42 days. At the end of its count binary counter 74 produces a carry out signal at a carry out terminal 74CO; the latter terminal is connected to a chip enable terminal 74 CET on counter 74 so that at the end of the count, the counter is inhibited from further counting thereby preventing destruction of the information stored in memory 78.

To permit recovery or read out of the data stored in the circuit, there is a multi-pin jack 81 which is accessible upon removal of bottom closure member 34. The jack has a pin 82 for an external clock pulse which typically has a relative fast repetition rate to afford rapid recovery of the data. There is a pin 84 for introducing a master reset signal in order that binary counter 74 can be reset to zero and caused to cycle through its count upon read out. Finally, there is a pin 86 for introducing a signal to memory 78 to retain the memory in a "read" mode and a pin connected to memory output 780.

As seen in FIG. 1, the components that form the counter circuit are mounted to individual circuit boards 88 and 90. The circuit boards are slidably received in respective cavities $C_{2b}$ and $C_{2c}$ so that they can be removed from container 12 for reuse after the pharmaceutical in compartment $C_1$ is expended. A cable 92 interconnects the components on the circuit boards and extends through compartment $C_{2a}$ below bottom wall 28.

In operation, container 12 and bottom wall 28 are cleaned, and the bottom wall is installed in spanning relation to the lower end of compartment $C_1$ and there fixed by adhesive 30. Next, reed switch 52 is installed in slot 50 with the leads thereof extending into cavities $C_{2b}$ and $C_{2c}$ through respective holes 54 and 56. A suitable hot melt adhesive is introduced into slot 50 to fix the reed switch in place and to form a surface flush with the surface of top wall 14, which facilitates placement of a label on the surface. Cap 40 is then installed after which the partially assembled container is sterilized such as by subjecting it to radiation of a suitable wave length and magnitude to render compartment $C_1$ sterile. Because cavities $C_{2b}$ and $C_{2c}$ are independently accessible, the circuit elements can be installed without destroying such sterile condition.

Independently of the foregoing, the circuit elements are assembled and tested after which circuit boards 88 and 90 and the components mounted thereon are potted in a suitable compound such as silicone RTV. The exterior shape of the potted units is such that they can be introduced into cavities $C_{2b}$ and $C_{2c}$ so as substantially to fill the respective cavities. The potted units are then introduced into the respective cavities, there being a socket on each of the units to effect connection with the leads of reed switch 52. Thereafter battery 60 is connected, terminal 84 is excited to reset the circuitry, and bottom closure 34 is fixed in place by staking or by adhesive. Finally, compartment $C_1$ is filled with a prescribed pharmaceutical and the container is delivered to a patient.

Because the counter circuitry is self contained, it is impossible for the patient to separate the circuitry from the pharmaceutical dispenser. Moreover, the container is completely portable, whether in pocket, purse or glove compartment because vibratory forces which might actuate mercury switch 58 will not be detected as an event by the counter circuit since the presence of cap 40 assures proximity between magnet 48 and reed switch 52 which prevents the contacts of the reed switch from opening. When the patient desires to administer the pharmaceutical within compartment $C_1$ it is necessary to remove cap 40 thereby causing the contacts within reed switch 52 to open. When housing 12 is inverted with cap 40 removed the contacts in mercury switch 58 open thereby supplying a signal to data input terminal 62 of flip-flop 64. Flip-flop 64, being a D-type flip-flop, retains that signal even after the contacts of reed switch 52 and mercury switch 58 are closed by replacing the cap and moving the housing to an upright position. The signal remains within flip-flop 64 until a clock pulse 72 occurs. With the occurrence of the clock pulse the output of NAND gate 76 is turned on which advances binary counter 74 by one count and therefore addresses a new memory cell within memory 78. Such clock pulse is transmitted through NAND gate 80 simultaneously to enable the data input terminal of the memory and to cause the data signal at terminal 62 of the flip-flop to appear at the output terminal 64Q thereof. Accordingly a signal is entered into the appropriate memory cell of memory 78 indicating that during the one hour interval preceding the occurrence of a clock pulse housing 12 has been inverted with the cap removed. If during a given one hour interval housing 12 was not inverted with the cap removed then no data input will occur on terminal 62 of the flip-flop whereupon the occurrence of clock pulse 72 will store no data signal in the memory cell that is addressed at that particular time.

The patient is instructed to return the container 12 to the clinician at some time, such as when the compartment $C_1$ is empty or after passage of a given time period. If the patient is tardy in so returning the container, no false signals occur because the counter has been inhibited from restarting its count at the end of the 1,024 clock pulses. In any even when the housing is returned, bottom closure member 34 is removed and a plug from readout equipment is connected to jack 80. Thereafter an external clock pulse is supplied to terminal 82 so as to cycle counter 74 through its count. The clock pulse can be at a much greater repetition rate than one per hour, so as to facilitate extraction of the data. Application of a read signal to terminal 86 causes the contents of the memory to be read out through the output 780 of a transistor that forms a part of memory 78. The data can be processed or displayed in any suitable manner to indicate the particular times during the period when container 12 was inverted with the cap removed, an event assumed to be concurrent with administration of the pharmaceutical by the patient.

The potted circuit components can be readily removed after removal of bottom closure 34 and battery 60. Housing 12 and cap 40 are relatively inexpensive parts and are discarded after use. The circuit components, however, can be reused after the data therein has been recovered.

Thus it will be seen that the invention provides a dispenser which affords to the clinician accurate information relating to compliance by the patient with dosage instructions. Because the counter circuitry is housed with the pharmaceutical in a single container, it is virtually impossible for the event of administration of the pharmaceutical not to be recorded. Moreover, the compactness of the apparatus is such that it is convenient for the patient to carry with him in virtually all situations. Finally, the dual compartmented construction of the housing is such that sterility is preserved without imposing stringent requirements on the counter circuitry or on the personnel installing such circuitry.

Although one embodiment has been shown and described it will be obvious that other adaptations and modifications can be made without departing from the true spirit and scope of the invention.

What is claimed is:

1. Apparatus for monitoring patient compliance with dosage instructions of a pharmaceutical comprising an impervious housing defining first and second mutually independent compartments, said housing including a neck defining a passage communicating with said first compartment to permit dispensing of the pharmaceutical from the first compartment through said passage, a cap removably engagable with said neck for selectively sealing said passage and said first compartment, an electronic counter disposed in said second compartment and having first and second inputs, said counter recording as an event only simultaneous excitation of said inputs, means responsive to removal of said cap for exciting said first input, and means responsive to movement of said housing to a position at which said neck is below said first compartment for exciting said second input so that said counter records the occurrence of each event when the housing is inverted with the cap removed.

2. Apparatus according to claim 1 wherein said electronic counter includes a memory having a plurality of addressable cells, timing means for producing a sequence of timing pulses at a preselected repetition rate, means connected to said timing means for addressing a unique cell in said memory in response to the occurrence of each said pulse, and gate means for connecting said first and second inputs to said memory in response to the occurrence of an event so as to afford storage of an event in the memory at an address corresponding to the time of occurrence of the event.

3. Apparatus according to claim 1 wherein said first input exciting means includes a permanent magnet disposed in said cap so as to produce a magnetic flux field on said housing when said cap is engaged on said neck, and flux sensitive means in said housing within said flux field for effecting excitation of said first input when the magnetic flux is removed from last said means in response to removal of the cap from the neck.

4. Apparatus according to claim 3 wherein said flux sensitive means comprises a magnetic reed switch having a pair of contacts that operate in response to impingement of magnetic flux thereon.

5. Apparatus according to claim 3 wherein said permanent magnet is of annular form and circumscribes said neck when said cap is engaged on said neck.

6. Apparatus according to claim 1 wherein said second input exciting means includes a gravity responsive switch switchable from a first electrical condition when said neck is above said first compartment to a second electrical condition when said neck is below said first compartment.

7. Apparatus according to claim 7 wherein said gravity responsive switch includes a mercury switch having first and second contacts and a quantity of mercury, said mercury bridging said first contacts when said neck is above said first compartment.

8. Apparatus according to claim 1 wherein said second compartment is of generally U-shaped configuration having first and second upright cavities and a lateral cavity extending between said upright cavities and establishing communication therebetween, said first compartment being disposed intermediate said upright cavities, said electronic counter having a first portion and a second portion disposed in respective said upright cavities, and a battery for energizing said electronic counter disposed in said lateral cavity.

* * * * *